US008097429B2

(12) United States Patent
Fodstad et al.

(10) Patent No.: US 8,097,429 B2
(45) Date of Patent: Jan. 17, 2012

(54) METHOD FOR CHARACTERIZATION OF ABNORMAL CELLS

(76) Inventors: Øystein Fodstad, Oslo (NO); Hanne Kleppe Høifødt, Hvalstad (NO)

( * ) Notice: Subject to any disclaimer, the term of this patent is extended or adjusted under 35 U.S.C. 154(b) by 861 days.

(21) Appl. No.: 11/047,913

(22) Filed: Feb. 1, 2005

(65) Prior Publication Data

US 2005/0130234 A1 Jun. 16, 2005

(51) Int. Cl.
*G01N 33/574* (2006.01)

(52) U.S. Cl. ........................................ 435/7.23; 435/7.1

(58) Field of Classification Search ........................ None
See application file for complete search history.

(56) References Cited

U.S. PATENT DOCUMENTS 4,511,662 A * 4/1985 Baran et al. .................. 436/513
5,340,719 A * 8/1994 Hajek et al. .................. 435/7.21

FOREIGN PATENT DOCUMENTS

WO WO 94/07139 * 3/1994

OTHER PUBLICATIONS

O'briant KC et al, 1991, Cancer, 68: 1272-1278.*
Mirro et al, 1985, Am J Clin Pathol, 83: 7-11.*
Wilkens, D.J, 1964, Nature, 202: 798-799.*
Tockman et al (Cancer Res., 1992, 52:2711s-2718s).*
Oesterreich, S et al, 1996 (Clin Cancer Res, 2: 1199-1206.*
Vandesompele J et al, 2003 (Oncogene, 22(3): 456-60).*
Bommer, KK, et al.; Fine-needle aspiration biopsy in the diagnosis and management of bone lesions: a study of 450 cases; Cancer, Jun. 25, 1997; 81(3); 148-56.
Cohen, M.C., Marven S., Walker J., Gerrard M.; A strategy for efficient handling of fresh tumor needle biopsies that allows histological and cytopathological assessment; Diagn. Cytopathol.; May 2008; 36(5); 285-9. Abstract Only.
Dalquen P., et al.; MIB-1 (Ki-67) immunostaining of breast cancer cells in cytologic smears; Acta. Cytol.; Mar.-Apr. 1997; 41(2); 229-37. Abstract Only.
Fekete PS, et al.; Fine-needle aspiration biopsy of the pancreas: a study of 61 cases; Diagn. Cytopathol.; Dec. 1986; 2(4); 301-6. Abstract Only.
Fulciniti F., et al.; Air-dried smears for optimal diagnostic immunocytochemistry; Act. Cytol.; Mar.-Apr. 2008; 52(2); 178-86. Abstract Only.
Khurana, KK, et al.; Diagnostic pitfalls of aspiration cytology of salivary duct carcinoma; Cancer Cytopathology; Nov. 2000; 81(6); 373-378.
Maksem, J, et al.; Endometrial collection and interpretation using the Tao brush and the CytoRich fixative system: a feasibility study; Diagn. Cytopathol; Nov. 1997; 17(5); 339-46. Abstract Only.
Payne PW, et al.; Sputum screening by quantitative microscopy: a reexamination of a portion of the National Cancer Institute Cooperative Early Lung Cancer Study; Mayo Clin. Proc.; Aug. 1997; 72(8); 697-704.
Raistrick J., et al.; Collection fluid helps preservation in voided urine cytology; Cytopathology; Apr. 2008; 19(2); 111-7. Abstract Only.
Ramos-Vara, J.A.; Technical aspects of immunohistochemistry; Vet. Pathol.; 2005; 42; 405-426.
Robb, J., et al.; Comparison of Cyto-Shuttle and cytocentrifuge as processing methods for nongynecologic cytology specimens; Diagn. Cytopathol.; Jun. 1996; 14(4); 305-9. Abstract Only.
Sauter ER, et al.; Nipple aspirate fluid color is associated with breast cancer; Cancer Detect. Prev.; 2006; 30(4); 322-8. Abstract Only.
Schindlbeck C, et al.; Immunomagnetic enrichment of disseminated tumor cells in bone marrow and blood of breast cancer patients by the Thomsen-Friedenreich-Antigen; Clin. Exp. Metastasis; 2008; 25(3); 233-40. Abstract Only.
Solomides CC, et al.; Semiquantitative assessment of c-erbB-2 (HER-2) status in cytology specimens and tissue sections from breast carcinoma; Anal. Quant. Cytol. Histol; Apr 1999; 21(2); 121-5. Abstract Only.
Spires SE, et al.; Assessment of cervicovaginal smear adequacy. The Bethesda System guidelines and reproducibility; Am. J. Clin. Pathol.; Sep. 1994; 102(3); 354-9. Abstract Only.
Tang CS, et al.; Alcoholic carbowax prefixation and formal alcohol fixation. A new technique for urine cytology; Acta. Cytol.; Jul.-Aug. 1997; 41(4); 1183-8. Abstract Only.

* cited by examiner

*Primary Examiner* — Misook Yu
*Assistant Examiner* — Lei Yao
(74) *Attorney, Agent, or Firm* — Stetina Brunda Garred & Brucker

(57) ABSTRACT

It is described a method to detect and phenotype target cells in cell suspensions by using particles coated with antibodies/ligands directed to antigenic determinants/receptors expressed on the target cells, characterized in that several types of particles, each particle coated with different antibody or ligand, are incubated simultaneously or subsequently with cell suspensions containing the target cells, in connection or not with a per se known enrichment procedure, a use of the method and a kit.

13 Claims, 2 Drawing Sheets

METHOD FOR CHARACTERIZATION OF ABNORMAL CELLS

Figure 1:
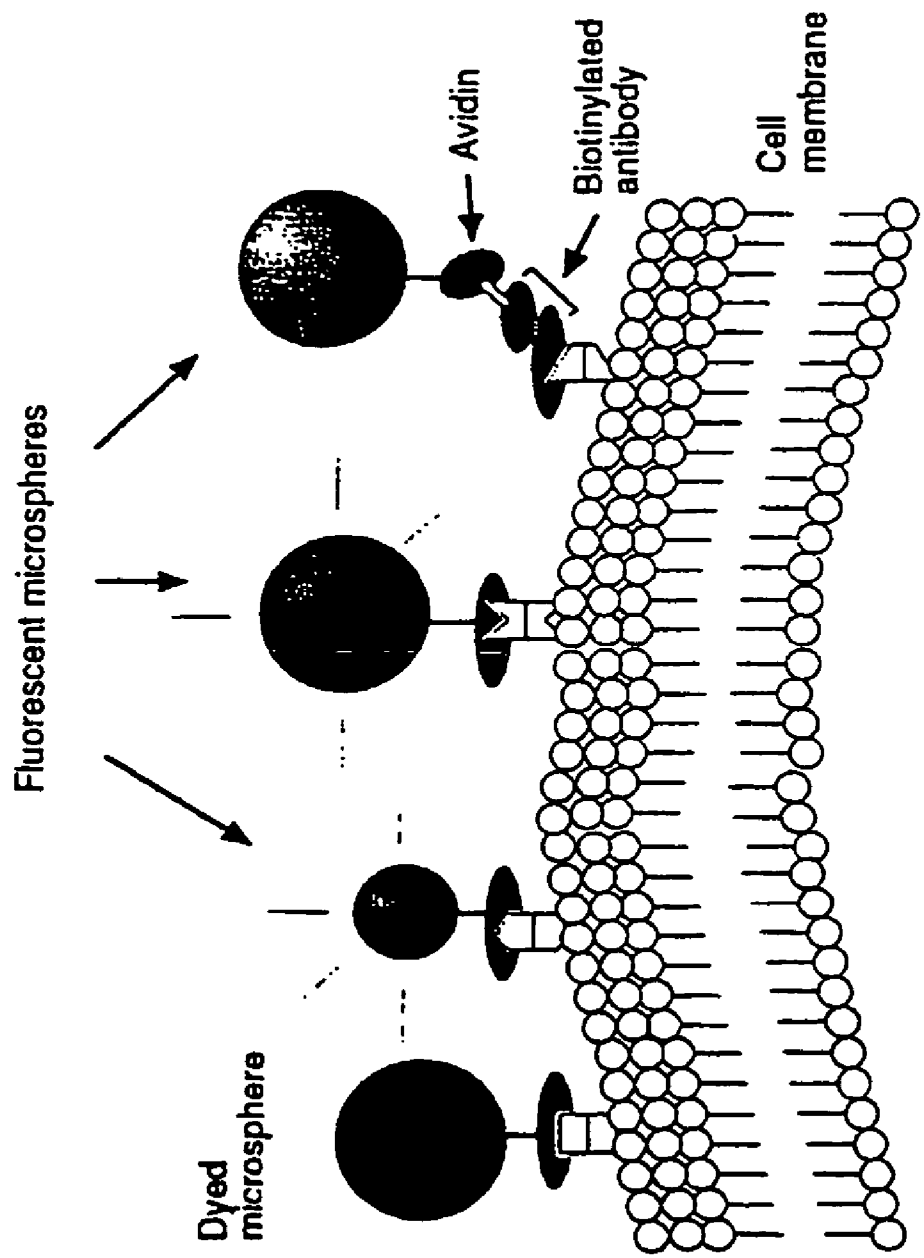

The present invention relates to a new method for identification and characterization of eukaryotic cells.

In several diseases such as primary and secondary malignancies, allergic, autoimmune, inflammatory, proliferative, infectious, and destructive disorders, or diseases for which the underlying mechanisms are unclear, it would be of utmost importance to be able to determine as many as possible characteristics of cells involved in the pathologic processes. An exact determination of a number of different markers on such cells would significantly improve diagnosis, prognostication and the choice of subsequent therapy. If such a procedure is simple and rapid, it would be easy to diagnose pathological conditions at an early stage of the disease, thereby increasing the probability of selecting the best therapeutic alternative at a time when the treatment may be most effective. Moreover, in some situations it is of crucial importance to make an immediate and correct diagnosis, such as to distinguish between a benign and a malignant tumor, to guide in the surgeons' selection of a proper operative procedure.

Presently, the following diagnostic methods related to the above mentioned pathological conditions are at hand: Conventional morphological examination of tissue sections, cell cytospins or smears, and immunological methods including immunocytochemistry, flowcytometry, and immuno-fluorescence microscopy. In addition, peroperative morphological evaluation of biopsied tissue specimens are performed on frozen sections.

With the non-immunological methods, the diagnosis can only provide distinction between normal and pathological cells based on morphological criteria.

Immunological methods such as immunocytochemistry and flowcytometry represent valuable diagnostic tools, although they suffer from several important limitations. With both methods, heterogenous cell populations are exposed to antibodies or other ligands for their binding to target cells. For flowcytometry studies live or fixed cells may be incubated to allow for fluorescence-labeled antibodies to bind to relevant membrane or intracellular antigens, before the cell suspension is analyzed in the instrument. Immuno-cytochemistry requires preparation of tissue sections, cytospins or smears, fixation and immunostaining of the cells before evaluation in a microscope. Visualization of bound antibodies is obtained indirectly through one or several steps ending with an enzyme/substrate color reaction, allowing the stained cells to be observed in a microscope. The multi-step procedure can not be completed on the day of cell sampling. Moreover, usually thorough evaluation by an experienced pathologist is needed for obtaining reliable results. For example, if the abnormal cells are being identified in a mixed cell population, and the ratio of pathological to normal cells is low, such as malignant cells in samples of bone marrow or peripheral blood, an exessive amount of work performed by a skilled pathologist may be needed for cell identification. Another problem is related to the fact that there are very few antibodies recognizing antigens that are selectively and consistently expressed in all target cells. If the objective is to identify tumor cells in blood and bone marrow, antibodies directed against "tissue-specific" markers, such as cytokeratins found in epithelial cells, are commenly used. However, as it is known that some normal cells may also express cytokeratins and that not all malignant epithelial cells do, there is a risk of both false positive and negative results.

Fluorescence-labeled antibodies can be used to detect target cells either by fluorescence microscopy or by flow cytometry. The former procedure can successfully be employed to demonstrate binding of a single antibody, although the use of morphological criteria as an additional way of distinguishing between normal and pathological cells is very limited. Moreover, the fluorescence usually fades and disappears rapidly under examination in the microscope. Thus, it is required that the fluorescence cells are studied and assessed microscopically within a short timeframe after binding of the antibody. Flowcytometric analysis requires the presence of a high number of target cells to provide reliable results. Moreover, the procedure does not provide any possibilities for morphological studies or for distinguishing between fluorescent target and non-target cells. Furthermore, several mentioned methods have the disadvantage that cells are lost in the methodological steps.

Improved possibilities for detecting target cells have recently been described (WO94/07138, WO94/07139, WO95/24648). In these procedures, antibodies bound to super-paramagnetic particles are used for detection and selection of the cells to be identified. One limitation of these methods is that it can be difficult to prove directly the pathological nature of cells with bound particles on the surface. One advantage compared to the other described methods is, however, the simplicity of the procedure and that results can be obtained within a very short timeframe.

To further confirm the pathologic nature of stained, fluorescent or immuno-bead-binding cells it is important to characterize the target cells for more than one marker. The aim is to obtain important biological information, and information of crucial diagnostic and prognostic significance. If the number of target cells is high, flow cytometry may be used to study in parallel the binding of two different cell-bound antibodies. However, this method lacks the possibility to examine individual cells and cell morphology, and actually to identify fluorescent cells as the real target cells. Immunocytochemistry does allow for a maximum of two markers to be studied in parallel, one with conventional enzymatic visualization of bound antibody and one with a silver/sold enhancement procedure. Both multi-step procedures are relatively complicated, time-consuming and requires either expensive equipment and/or special expertise in the respective areas.

With the immunomagnetic method, further characterization of whole cells may be obtained by preparing cytospins of the magnetically selected cells and thereafter performing immunostaining as for conventional immuno-cytochemistry. Therefore, the same limitations as described for immunocytochemistry apply, and furthermore because the target cells have beads attached to their surface it may be difficult to get the cells to stick to the slides used for conventional cytospin preparation.

U.S. Pat. No. 5,340,719 discloses an optical screening method in which the cells are combined with one or more different sets of microspheres differing in colour or size.

WO 94/07142 discloses an assay for the presence and relative abundance of T-lymphocyte subpopulations using different antibodies attached to a different particle. Both methods are used to isolate haematopoetic cells without specificity requirements and employ methodological steps increasing the risk for damaging the target cells.

In conclusion, the existing methods provide possibilities for studying a maximum of two independent markers, and inherent to the described methods several important problems and limitations are present. It was therefore desireable to develop a method that much more simply, rapidly, and reliably could help identifying and characterizing target pathological cells. The complexity and heterogeneity of cell biology makes it also necessary to be able to examine expression of several independent biological markers on the same cells. Such biological information would be of vital diagnostic and prognostic significance that can aid in the choice of therapeutic alternative. When several markers are examined in parallel it would be possible to obtain a more reliable confirmation of the pathological nature of the target cells, thereby improving the diagnostic reliability and help excluding false positives as well as negatives. Importantly, multi-parameter characterization could include markers of cell proliferation, cell death (such as apoptosis), adhesion, motility, invasion, antigenicity, inflammation, cell destruction, auto-immune mechanisms, angiogenesis, disease agressiveness, tumor metastasis, and inhibitors of all these functions. Furthermore, if several markers can be examined also at an individual cell level, it would be possible to study cell heterogeneity and identifying subsets of cells with specific biological properties. In some diseases it would also be important to study pathological cells obtained from different sites in the same patient in order to determine whether cell characteristics could vary from one site to another, thus providing additional biologically and prognostically important information. Altogether, the impact of obtaining information of the type here described for clinical evaluation and treatment of patients can hardly be overestimated.

These objects are obtained in the present invention as characterized by the enclosed claims.

We here introduce a new concept in characterization of intact target cells in cell suspensions, making a direct microscopical identification of more than two membrane-associated markers possible. With this method several cell membrane markers of the origin, biology and potential fate of target cells can be studied in the same operation. The procedure is very simple and can be completed within a very short timeframe without the need for advanced and eexpensive instrumentation. With the method, target cells can with a minimum of handling steps, without any cell loss, be studied microscopically for the expression of several independent marker molecules, even at the individual cell level. Thus, in addition to obtaining an overall picture of biological parameters present in the target cell population, such a procedure also allows for examining cell to cell variation in the expression of marker molecules, providing information with vital biological and medical implications.

Briefly, the method can be performed as here described: Dyed or fluorescent microspheres (beads, particles) conjugated with antibodies or ligands that can bind to cell membrane determinants to be studied are added to the cell suspension and incubated under gentle rotation. Thereafter, samples of the cell suspension are examined in a fluorescence microscope for cells with surface-bound microspheres of different light or fluorescent colors. The extent and variation in cell binding of the different microspheres can be assessed and quantitated. The assessment of cell-bound particles may, if desired, be performed by an automized procedure.

In the following the present invention is described in greater detail with the examples, which by no means are intended to restrict the invention, and figures in which:

FIG. 1 illustrates the binding of four types of microspheres to four different antigenic determinants expressed on the membrane of a target cell. The binding is in this case mediated through four different antibodies each recognizing one of the said four antigens, in that the antibodies had first been conjugated to the respective microspheres, either directly through a chemical bond (FIG. 1, the three examples to the left), or indirectly where the beads had been pre-coated with avidin before conjugation to a biotinylated antibody (FIG. 1, right example). As illustrated in FIG. 1, one antibody was bound to a blue dyed microsphere, one antibody to a small and another to a larger red fluorescent microsphere, whereas the fourth antibody had been biotin-avidin conjugated to a green fluorescent microsphere.

Figure 2:
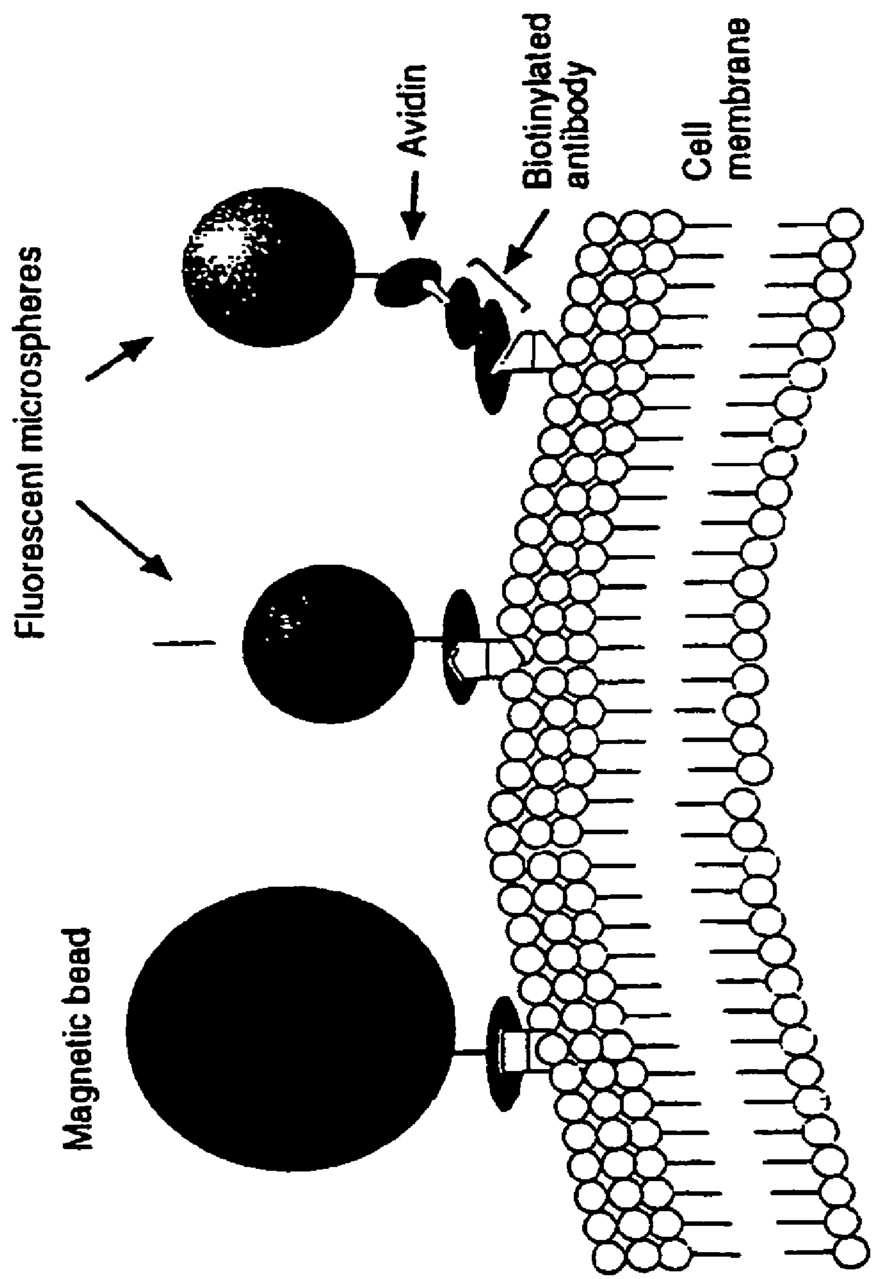

FIG. 2 illustrates how the invention can be used to characterize two or more cell membrane determinants in a situation where the target cells in a mixed cell suspension are rare, thus warranting an enrichment procedure before evaluation of the sample. In the illustrated case, antibody coated super-paramagnetic beads are bound to the cell membrane together with red and green fluorescent microspheres conjugated either directly or through an avidin-biotin binding to separate antibodies. In such a situation, immuno-magnetic enrichment can be obtained by using a strong magnet that will atract cells with bound magnetic beads. The enriched cell suspension is thereafter examined in a microscope in which the binding of the fluorescent microspheres to target cells with bound magnetic beads can be observed.

The visually or instrumentally different dyed or fluorescent particles, which can be of similar or different sizes, used in the invention are conjugated to ligands such as antibodies, or fragment of antibodies, lectins and growth factors, that can bind to specific molecules expressed on membranes of abnormal cells, so that the bound particles can be identified microscopically. Examples include the use of polystyrene latex fluorescent microspheres of various colors that can be observed in a fluorescence microscope, and dyed non-fluorescent particles, such as red, yellow, green, black and blue, that can be detected by light microscopy. Antibodies conjugated to the microspheres include all those recognizing antigens, receptors, and other determinants expressed on membranes of abnormal cells, and on normal cells, see below. By combining different antibody-particle conjugates relevant for the cells to be studied, a finger-print of cell characteristics can be obtained rapidly and directly in the cell suspension. Such antigenic finger-prints would be highly valuable in evaluating important biological characteristics of cells, see above, cell populations or sub-populations. The simplicity and speed by which the method can provide such information is surprising and constitutes a key element of the invention.

Antibody-conjugated fluorescent and dyed particles have been used in various types of immunoassays to determine, e.g. the presence of free antigens, proteins, viruses and bacteria in biological fluids. With intact eukaryotic cells, fluorescent microspheres conjugated to antibodies have been used to study in each case a single molecule expressed in a specific type of normal cells, such as monocytes, lymphocytes, hepatocytes and fibroblasts. The purpose of these studies have been such as examination of the motility of membrane markers in macrophages or metabolic parameters in hepatocytes. There is no report found in the literature on attempts to study abnormal cells, such as malignant and benign neoplastic cells, and abnormal cells found in various infectious, reactive, autoimmune, inflammatory and proliferative disorders. Furthermore, combination of several antibodies conjugated to different dyed or fluorescent microspheres on the same cell population, or on individual cells, are not described. Also, such procedures have not been employed to study, for biological or diagnostic purposes, sub-populations of target cells in a mixed population of cells.

The particles to be used can be fluorescent polystyrene latex microspheres or non-fluorescent particles of different colors. The size of the microspheres can be between 0.01 μm and 6 μm The particles should provide possibilities for conjugating antibodies or other ligands to their surface. This may be obtained directly, such as through chemical groups like carboxyl, amino or other groups, or indirectly by binding antibodies to microspheres previously coated with proteins such as avidin, streptavidin, protein A, or with antibodies that can react with a second antibody. The size of the microspheres may be chosen to fit the size of the cells and the purpose of investigation, such that it would facilitate identification of different bound antibody-microsphere conjugates. It is considered that a particle size of e.g. 1 μm makes identification of a relatively low number of bound particles easy, whereas a smaller size may possibly be advantageous if a marker protein expressed at high density is to be studied. Another important feature of the invention is that it can be applied both when a very low or a very high number of cells are to be examined. It is also important that the fluorescent microspheres can retain their fluorescence strength for a considerable length of time.

The antibodies recognizing the relevant membrane marker antigens or receptors could either be whole IgG of any isotype, IgM antibodies or any fragments of such antibodies, including also recombinant antibodies or antibody fragments. The novel method includes binding of the said fluorescent or dyed microspheres to target cells in a suspension with a low number of non-target cells, and in other cases where the number of target cells is low compared to non-target cells. The cell suspension is incubated with several antibodies, preferably 2-6, each conjugated to different microspheres, of the same or different sizes, of a specific dye or fluorescent color. The ratio between the number of particles and the number of target cells ranges from 20:1 to 0.5:1, preferably 5:1, limited by the size of the particles. The cell suspension should be incubated with antibody-coated beads for 5-10 minutes to 2 hours, preferably for 30 minutes, at 0°-37° C., preferably at 4° C. under gentle rotation. After incubation, samples of the cell suspension is taken for evaluation in a fluorescence microscope or in other visualizing or imaging devices in which fluorescent particles and dyed particles can be observed. Microspheres that are bound to cells can then be visualized, and the number of cells with the different types of particles attached to their surface can be assessed, with or without enumaration also of the number of beads attached to the cells. Since it is possible to use a combination of several antibody-coated microspheres, fluorescence filters suited to study different fluorescence emission spectra may be used. The method also provides possibilities for semi-automatic, video, and computer image analysis of the presence of dyed or fluorescent particles bound to the cells.

The antibodies could be of murine, rat, rabbit or human origin and may preferably recognize antigens present on target cells and not on normal cells in mixed cell suspensions. A list of antibodies/ligands includes, but are not limited to, those directed against groups of antigenic determinants, for example CD56/NCAM antigen, pan-epithelial EGP2/cluster2 antigen, breast mucin (MUC1) and other mucin epitopes, HMW and other melanoma-associated antigens such as gp100, MAGE 1, 2 and 3, and MUC18, 80 kD sarcoma associated antigen, erbB2, receptors for growth factor such as EGF, TGF, PDGF, bFCF, VEGF, IGF1, and IGF2, laminin, laminin5, uPA, uPAr, PAI, TIMP1 and 2, stromelysin, and other invasion related molecules. CEA, PSA, PSM, NSE, c-Met, CD44 and variants, ICAM-1, integrins, cadherins, catenins and other cell adhesion-associated molecules, drug resistance markers such as MDR and MRP, apoptosis-related molecules such as Fas and FasL, markers of cell proliferation, motility, differentiation, metastasis, angiogenesis, signal transduction, and inflammation-related membrane molecules, oncogene products, and chemokine receptors such as CCR 1-5, CXCR 1-4, and Duffy antigen, and all types of hematopoietic and lymphatic cell markers categorized in the CD system. Table 1 lists groups of membrane determinants that can be targeted and a number of examples within each group is also presented.

TABLE 1

Antigens/receptors and cooresponding antibodies/ligands

| ANTIGENS/RECEPTORS | EXAMPLES OF ANTIBODIES/LIGANDS |
|---|---|
| Adhesion molecules | |
| Integrins | Pierce 36114, BTC 21/22, M-Kiol 2<br>BTC 41/42, Calbiochem 407277-84 |
| ICAM-1 (CD54) | C57-60, CL 203.4 |
| VCAM-1 | Genzyme 2137-01 |
| HCAM | BCA 9 |
| LCAM | BM 1441 892 |
| ELAM-1 | Genzyme 2138-01 |
| E-selectin | BBA 8 |
| P-selectin | BTC 71/72 |
| LFA-3 (CD58) | TS 2/9 |
| MACAM-1 | NKI-M9 |
| E-cadherin | BTC 111, 6F9 |
| P-cadherin | NCC-CAD-299 |
| Tenascin | BM 1452 193 |
| Thromobspondin receptor (CD36) | BM 1441 264 |
| VLA-2 | A1.43 |
| Carbohydrate antigens | |
| T-antigen | HH8, HT-8, Lectins |
| Tn-antigen | TKH6, BaGs2, Lectins |
| Sialyl Tn | TKH-2 |
| Galbl-4GlcNaC (nL4, 6, 8) | 1B2, Lectins |
| Gastroinestinal cancer associated antigen (M.200kD) | CA 19-9 |
| $Le^y$ | MLuC1, BR96, BR64 |
| di-$Le^x$, tri-$Le^x$ | B3 |
| CA15-3 epitope | CA15-3 |
| CEA | I-9, I-14, I-27, II-10, I-46, |
| Lacto-N-fucopentanose III (CD15) | PM-81 |
| Glycolipids | |
| $GD_3$ | ME 36.1, R24 |
| $GD_2$ | ME 36.1, 3F8 |
| $Gb_3$ | 38-13 |
| $GM_3$ | M2590 |
| $GM_2$ | MKI-8, MKI-16 |
| $FucGM_1$ | 1D7, F12 |
| Growth factor receptors | |
| EGF receptor | 425.3, 2.E9, 225 |
| c-erbB-2 (HER2) | BM 1378 988, 800 E6 |
| PDGFα receptor | Genzyme 1264-00 |
| PDGFβ receptor | Sigma P 7679 |
| Transferrin receptor | OKT 9, D65.30 |
| NGF receptor | BM 1198 637 |
| IL-2 receptor (CD25) | BM 1295 802, Bm 1361 937 |
| c-kit | Bm 428 616, 14 A3, ID9.3D6 |
| TNF-receptor | Genzyme 1995-01, PAL-M1 |
| NGF receptor | |
| Melanoma antigens | |
| High molecular weight antigen (HMW 250.000) | 9.2.27, NrML5, 225.28 |
| Mw105 melanoma-associated glycoprotein | ME20 |
| 100 kDa antigen (melanoma/carcinoma) | 376.96 |
| gp 113 | MUC 18 |
| p95-100 | PAL-M2 |
| gp75/TRP-1 | 15.75, TA99 |
| gp 100-107 | NKI-beteb |
| MAA | K9.2 |
| M125kD (gp125) | Mab 436 |

TABLE 1-continued

Antigens/receptors and cooresponding antibodies/ligands

| ANTIGENS/RECEPTORS | EXAMPLES OF ANTIBODIES/LIGANDS |
|---|---|
| MAGE 1, 2, 3 | anti-MAGE 1, 2, 3 |
| Tyrosinase | anti-tyrosinase |
| Sarcoma antigens | |
| TP-1 and TP-3 epitope | TP-1, TP-3 |
| M.200kD | 29-13, 29.2 |
| M.160.kD | 35-16, 30-40 |
| Carcinoma markers | |
| EGP-2 (cluster 2 epithelial antigen) | MOC-31, NrLu10 |
| MUC-1 antigens (such as DF3-epitope (gp290kD) | BM7, DF3, BCP-7 to −10 |
| MUC-2 and MUC-3 | PMH1 |
| LUBCRU-G7 epitope (gp 230kD) | LUBCRU-G7 |
| Prostate specific antigen | BM 1276 972 |
| Prostate cancer antigen | E4-SF |
| Prostate high molecular antigen M. > 400kD | PD41 |
| Polymorphic epithelial mucins | BM-2, BM-7, 12-H-12 |
| Prostate specific membrane antigen (Cyt-356) | 7E11-C5 |
| Human milk fat globulin | Immunotech HMFG-1, 27.1 |
| 42kD breast carcinoma epitope | B/9189 |
| $M_w > 10^6$ mucin | TAG-72, CC-49, CC-83 |
| Ovarian carcinoma OC125 epitope (m. 750 kD) | OC125, OVX1 |
| Pancreatic HMW glycoprotein | DU-PAN-2 |
| Colon antigen Co-17-1A (M.37000) | 17-1A |
| Ga 733.2 | GA733, KS1.4 |
| TAG 72 | B72.3, CC-49, CC-83 |
| Pancreatic cancer-associated | MUSE 11 |
| Pancarcinoma | CC49 |
| Prostate adenocarcinoma-antigen | PD 41 |
| $M_w$ 150-130kD adenocarcinoma of | AF-10 |
| $M_w$ 92kD bladder carcinoma | 3G2-C6 |
| $M_w$ 600kD bladder carcinoma | C3 |
| Bladder carcinoma antigen | AN43, BB369 |
| Hepatocellular carcinoma antigen M.900kD | KM-2 |
| $M_w$ 48kD colorectal carcinoma | D612 |
| Colon specific antigen | Mu-1, Mu-2 |
| Lung carcinoma antigen M. 350-420kD | DF-L1, DF-L2 |
| Colon cancer-associated | C242, NCRC37 |
| Bladder carcinoma antigens | T16, T43, T138 |
| Neuroblastoma antigen | |
| Neuroblastoma-associated, such as UJ13A epitope | UJ13A |
| Glioma antigens | |
| Mel-14 epitope | Mel-14 |
| HMW 250kD | 9.2.27 |
| Head and neck cancer antigens | |
| M.18-22kD antigen | M48 |
| HLA-antigens | |
| HLA Class 1 | TP25.99 |
| HLA-A | VF19LL67 |
| HLA-B | H2-149.1 |
| HLA-A2 | KS1 |
| HLA-ABC | W6.32 |
| HLA-DR, DQ, DP | Q 5/13, B 8.11.2 |
| $\beta_2$-microglobulin | NAMB-1 |
| Apoptosis associated molecules | |
| Fas (CD95/APO-1) | Apo 1 |
| FasL | Anti-FasL |
| P75 | NGF |

TABLE 1-continued

Antigens/receptors and cooresponding antibodies/ligands

| ANTIGENS/RECEPTORS | EXAMPLES OF ANTIBODIES/LIGANDS |
|---|---|
| Various | |
| cathepsin D | CIS-Diagnostici, Italy |
| neuroglandular antigen | ME91, NKI-C3, LS62 |
| pan-human cell antigen | pan-H |
| Motility related antigens | anti-KAI-1, anti-AMF |
| Proliferation-associated markers | anti-gp120, anti-Ki-67 |
| Differentiation-associated markers | MUC 18, TA99 |
| Drug resistant-related markers | C 219, MRK 16, anti-MRP |
| Angiogenesis-associated markers | anti-VEGF, anti-bFGF |
| Chemokine receptors markers | anti-CCR, anti-CXCR |
| Invasion-related antigens | Antibodies to: PAI, MMP1, MMP9, TIMP1, TIMP2, laminin V, stromelysin, uPAR, uPA |

The examples described below illustrates embodiments and reflect the potential of the new method for detection and characterization of target cells, not previously known by persons with knowledge in the art. It was highly surprising that mixed cell populations could be incubated simultaneously, or subsequently, with a number of different particle-bound antibodies, that for each antibody the binding of the antibody-particle complex to the target cells was specific and that the binding of different complexes could easily be visualized and distinguished in a fluorescence microscope with individual and/or several filters compatible with fluorescent emission spectra of the fluorescent microspheres, or by changing to conventional light microscopy to better identify binding of dyed non-fluorescent beads.

When several antibody-particle complexes are simultaneously incubated with target cells in a mixed cell suspension, one would easily have expected that the complexes could cluster or otherwise react with each other, forming complexes that unspecifically might bind to cells, that they for sterical or other reasons could block each others binding to target antigens, or that the fluorescence of the particles could be quenched, making it difficult to distinguish between the different types of particles. Surprisingly, however, by following the procedure according to the invention, no such problems are observed. The specificity of this approach is further demonstrated in experiments that included incubation of the target cells with one antibody-particle conjugate that would yield yellow fluorescence in the microscope, and thereafter with the same antibody coupled to a particle with a red fluorescence. In this case binding of the yellow antibody-particle conjugate was observed, whereas the binding of the second complex was completely blocked since the same antibody had been used for conjugation to both the yellow and the red particles.

In cases where the target cells in a mixed cell suspension are rare, such as tumor cells in peripheral blood and bone marrow, an enrichment procedure may be introduced before or in combination with the color/fluorescent-particle procedure. The enrichment can be obtained with different previously known approaches, including immunological procedures such as panning, column separation, or immunomagnetic positive or negative selection. If immunomagnetic selection is preferred, the same incubation step may include both the magnetizable and non-iron containing beads with the relevant cell binding antibody. After the enrichment step, the cell suspension containing the target cells can be examined and microscopically evaluated for fluorescent or dyed particle binding. Moreover, if immunomagnetic beads of a size of for example at least 1 μm are used for enrichment, such cell-bound beads can also be observed and used as an additional cell marker (FIG. 2).

The possibility of having a rapid, simple and reliable way of simultaneously mapping expression patterns of several relevant markers on cell populations, or at an individual cell level, opens new avenues in cell biology research and for routine diagnostic, staging and prognostic evaluation of a wide range of diseases, originating in all types of human and animal tissues. In many circumstances a rapid diagnosis is of great importance in the choice of therapeutic alternative. Examples of this includes surgical procedures to be chosen depending on whether e.g. a mammary, prostate or a brain tumor is malignant or not, whether a lymph node enlargement is caused by tumor cell infiltration or by an inflammatory reaction, on what type of cells that constitute thickening of synovial membranes in joints, what of type of cells that are present in surgical, needle, or fiberoptic biopsies from lesions in the skin, lung, liver, bone, ovaries or in the instestine and other tissues, and on what type of cells that might be present in pleural or ascitic effusions, in CSF, lymph, peripheral blood and bone marrow. At present, diagnosis of such cells are mainly based on morphological evaluations, and also on immunocytochemistry performed after preparation of tissue sections, cytospins or smears. Morphologically it can be difficult to determine the nature of the cells, and as previously mentioned immunocytochemistry can maximally detect the presence of two markers. With the new method, cells from the samples are dispersed e.g. in physiological saline or medium, incubated with relevant antibody-microsphere combinations for the necessary length of time, usually 30 minutes, and then examined microscopically. In the cell suspension, the bound particles can easily be recognized, permitting a suprisingly rapid and simple immunological fingerprinting or profile of the target cells. Because of this simplicity, the multiparameter characterization, the very short time frame needed to complete both the procedure and evaluation, the method represents a major contribution in the efforts to achieve rapid and reliable diagnosis of disease and obtain information of crucial importance for the further handling of patients.

To illustrate situations where such characterization is important the following teoretical examples are included:

In breast cancer it is known that the expression on the tumor cells of markers such as erbB2, EGF receptor, and IGF2 may be associated with increased proliferation and agressiveness of the disease. In addition, the expression of other determinants such as EGP2, uPAr, VEGF, MUC1, MDR, Fas, and FasL can reflect characteristics that are important for the ability of the cells to metastasize, to induce angogenesis, to resist chemotherapy, as well as for apoptosis of the tumor cells or the host T-cells. By using a combination of microspheres several of these parameters can be registered simultaneously in only one operation. Such studies can be performed on the biopsies from the primary tumor, on needle biopsies from solid metastases, and on samples from ascitic or pleural effusions, blood, and bone marrow.

In HIV-infected patients, the characterization of the different subsets of T lymphocytes is of vital importance. Examples of determinants that with the new method can be studied in addition to the most common T-cell markers are chemokine receptors and apoptosis-related molecules such as Fas and FasL.

In malignant melanoma the degree or lack of differentiation of the tumor cells may relect the potential agressiveness of the disease in the way that lesser differentiation is related to increased malignancy. In addition, several molecules are important for immunological response, including markers such as gp100, MAGE1, 2, 3, B7, Fas and FasL. Since such markers are important for the effect of immunotherapy and vaccination, comprehensive characterization of these as well as other melanoma-associated antigens are of great importance for the clinical management of the patients. Such characterization can readily be done with the new procedure.

Lymph node enlargement can reflect different types of reactive, infectious, or malignant conditions. Thus, it may be important to determine whether such lymph nodes contain tumor cells or not. If tumor cells are present, determination of the type of malignant cells can decisively influence the choice of therapy. One example is lymph node metastasis that could originate from either a small cell lung cancer (EGP2) or a malignant melanoma (HMW250000). With the appropriate choice of antibody-microsphere conjugates this distinction can easily be made with the new approach within less than one hour.

EXAMPLES ON THE USE OF THE NEW PROCEDURE

1. Specificity Testing of Antibody-Conjugated Fluorescent Particles in Human Breast Cancer Cells.

MCF-7 human breast cancer cells were incubated with 1 μm bright pink fluorescent microspheres coated with avidin, with or without biotin-conjugated MOC31 anti-EGP2 (anti-epithelial cell marker) antibody, and/or with immunomagnetic beads (4.5 μm) coated with an anti-breast mucin (MUC1) antibody (BM7).

A suspension of MCF-7 cells incubated with fluorescent particles without bound MOC31 antibody was examined in a microscope. No fluorescent beads were attached to the tumor cells. Similar experiments with MOC31 biotin-avidin-conjugated fluorescent particles showed from 5 to 10 fluorescent particles bound to the surface of the tumor cells. In other experiments, MCF-7 cells were incubated with immunomagnetic beads coated with the BM17 antibody that bind to the tumor cells, followed by incubation with fluorescent particles with and without MOC31 antibody. It was found that the tumor cells with surface bound immunomagnetic beads showed binding also and only of MOC31-conjugated fluorescent particles. The two types of particles could easily be used in parallel, and the results showed no unspecific cell adherence of particles lacking targeting antibody.

2. Effect of Simultaneous or Subsequent Incubation with Antibody-Coated Beads

Human SKBr3 breast cancer cells were incubated with various combinations of bright pink fluorescent latex microspheres conjugated with MOC31 antibody, with or without simultaneous or subsequent incubation with immunomagnetic beads coated either with MOC31 or with BM7 antibodies. Bead sizes as in example 1. If both the fluorescent and immunomagnetic beads had the same targeting antibody and were incubated simultaneously, both types of beads were seen bound to the tumor cells. If either of these microspheres/beads were incubated first for 30 min and thereafter for another 30 min with the other antibody-conjugated particles, the binding of the second antibody-particle complex was completely blocked. The binding of each type of beads conjugated with different antibodies and incubated simultaneously showed the same binding pattern as that seen if each of them were studied in separate experiments.

3. Simultaneous Binding of Several Types of Microspheres/Beads to the Same Target Cells.

Breast cancer cells known to express a number of different antigens on their surface were incubated simultaneously with antibodies recognizing four different of these antigens. Each antibody had independently been conjugated to four types of microspheres/beads: 1) blue dyed latex microspheres (0.5 μm), 2) bright pink fluorescent latex microspheres (1 μm), 3) yellow fluorescent microspheres (1 μm), and 4) immunomagnetic super-paramagnetic particles (4.5 μm). The method according to the invention showed that the tumor cells did bind all the four different types of beads which could be clearly recognized by using a combination of fluorescence and light microscopy. The number of particles attached to each cell varied for each antibody-particle complex in accordance with the known expression pattern of the corresponding antigen. The antibodies recognized the following antigens: EGP2, MUC1, EGF receptor, and an independent epithelial marker recognized by the 595 antibody.

4. Binding of Fluorescent Microspheres on Target Cells after Immunomagnetic Enrichment.

MCF7 human tumor cells were added to mononuclear peripheral blood cells from healthy volunteers in a ratio of 1/1000 tumor cells to mononuclear cells. The cell suspension was incubated with MOC31 anti-epithelial antibody attached to bright pink fluorescent microspheres (1 μm) through an avidin/biotin bond and simultaneously with super-paramagnetic immunobeads (4.5 μm) coated with the BM7 anti-MUC1 antibody. After 30 min of incubation magnetic selection of tumor cells with immunomagnetic beads bound to their surface was performed, and samples of the resulting cell suspension was examined microscopically. It was found that the remaining tumor cells with bead rosettes on their surface had also bound 5-10 fluorescent particles to the membrane, whereas a contaminating normal cells did not show binding of any of the particles/beads.

5. Binding of Fluorescent Cells to Malignant Ascitic Cells

A suspension of ascitic cells drawn from a patient was brought to the laboratory without any information of the origin of the cells. The cell suspension was incubated with different antibody-coated fluorescent particles and paramagnetic immunobeads according to the invention. Particles coated with antibodies recognizing different marker antigens bound to the cells in the suspension, demonstrating the malignant and epithelial nature of the cells, thus confirming the diagnosis of ovarian cancer. In another case with ascitic fluid no cells with antibody-coated particles were seen, in agreement with the conclusion of the referring pathologist. In both cases, the method described in the invention provided the results on several different markers within 45 minutes, whereas the parallel morphological and immunocytochemical examination of a single marker was first completed more than 24 hours later.

6. Detection of Cells in a Pleural Effusion

Without any prior knowledge of the underlying disease, incubation of the cell suspension with different anti-tumor antibodies coated onto fluorescent and immunomagnetic particles showed strong binding of all microspheres and immunobeads with anti-carcinoma and breast mucin (MUC1) antibodies. The diagnosis of the patient was breast cancer with pleural effusion. Microspheres conjugated with an anti-melanoma antibody did not bind. In conclusion, also in this case the cells in the clinical sample were successfully identified.

7. Needle Aspirate from a Thyroid Tumor

The cell suspension obtained from needle aspirate was incubated with fluorescent microspheres with an antibody known to react with colorectal cancer cells, and simultaneously with immunomagnetic beads coated with the MOC31 anti-epithelial antibody. The fluorescent microspheres did not bind to any types of cells in the suspension, whereas the MOC31 immunobeads bound strongly to thyroid epithelial cells but not to the high number of macrophages present in the suspension.

The above examples demonstrate that the new method according to the invention shows considerably increased diagnostic strength and reliability in that a higher number of target cell antigenic determinants can be deleted in one operation, in a very short period of time compared to previously known methods.

The invention claimed is:

1. A method to diagnose a disease state in a patient, by detecting and phenotyping live target cells in cell suspensions to determine an antigenic finger-print of the live target cells, the method using particles coated with antibodies directed against antigenic determinants/receptors expressed on the target cells, wherein the method comprises:

incubating 2 to 6 antibodies under gentle rotation for about 5 minutes to about 2 hours with cell suspensions containing the live target cells at 0° C. to 25° C., all of the antibodies being directed against independent antigenic determinants/receptors expressed on the same cells, wherein each antibody is conjugated to a visually different fluorescent or dyed non-fluorescent particle with at least one of the particles being a fluorescent particle and at least one of the particles being a dyed non-fluorescent particle, said particles capable of being instrumentally or visually separated from the other particles by differing sizes, fluorescent emission spectra, and/or colors, each particle ranging in size from about 0.01 μm to about 6 μm, wherein the ratio between the number of particles and the number of cells ranges from about 0.5:1 to about 20:1; followed by an enrichment procedure that enriches the cell suspensions for the live target cells; and diagnosing the disease state by determining the antigenic fingerprint of the live target cells via evaluation of the live target cell rosettes microscopically by fluorescence microscope visualizing or imaging devices, and evaluating the antigenic fingerprint to determine the presence or absence of the disease state.

2. The method according to claim 1, wherein the size of the particles ranges from 0.5 μm to 4.5 μm, the ratio of number of particles to number of cells is 5:1, the incubation time is 30 minutes and the incubation temperature is 4° C.

3. The method according to claim 1, wherein the particles used are coated with antibodies directed against the receptors/antigens selected from the group consisting of integrins, ICAM-1 (CD54), VCAM-1, HCAM, LCAM, ELAM-1, E-selectin, P-selectin, LFA-3 (CD58), MACAM-1, E-cadherin, P-cadherin, Tenascin, Thrombospondin receptor (CD36), VLA-2, NCAM (CD56), CD44, CD44 variants, T-antigen, Tn-antigen, Sialyl Tn, Galbl-4GlcNac (nL4, 6, 8), Gastrointestinal cancer antigen, $Le^y$, tri-$Le^x$, CA15-3 epitope, CEA, Lacto-N-fucopentanose III (CD15), $GD_3$, $GD_2$, $Gb_3$, $GM_3$, $GM_2$, $FucGM_1$, EGF receptor, c-erbB-2 (HER2), PDGFα receptor, PDGFβ receptor, Transferrin receptor, NGF receptor, IL-2 receptor (CD25), c-kit, TNF-receptor, high molecular weight melanoma antigen (HMW 250,000), MW 105 melanoma glycoprotein, 100 kDa antigen (melanoma/carcinoma), gp 113, p95-100, gp75/TRP-1, gp 100-107, MAA, MW 125 kD (gp125), MAGE 1, MAGE 2, MAGE 3, Tyrosinase, TP-1 epitope, TP-3 epitope, MW 200 kD sarcoma antigen, MW 160 kD sarcoma antigen, EGP-2 (cluster 2 epithelial antigen), MUC-1 antigens, MUC-2, MUC-3, LUBCRU-G7 epitope (gp 230 kD), Prostate specific antigen, Prostate cancer antigen, Prostate high molecular antigen (MW>400 kD), Polymorphic epithelial mucins, Prostate specific membrane antigen (Cyt-356), Human milk fat globulin, 42 kD breast carcinoma epitope, MW>$10^6$ mucin, Ovarian carcinoma OC125 epitope (MW 750 kD), Pancreatic HMW glycoprotein, Colon antigen Co-17-1A (MW 37,000), Ga 733.2, TAG 72, Pancreatic cancer antigen, Pancarcinoma antigen, Prostate adenocarcinoma-antigen, MW 150-130 kD adenocarcinoma antigen, MW 92 kD bladder carcinoma antigen, MW 600 kD bladder carcinoma antigen, Bladder carcinoma antigen, Hepatocellular carcinoma antigen, MW 48 kD colorectal carcinoma, Colon specific antigen, Lung carcinoma antigen MW 350-420 kD, Colon cancer antigen, Bladder carcinoma antigens, Neuroblastoma antigen, Mel-14 epitope, HMW 250 kD glioma antigen, MW 18-22 kD head and neck cancer antigen, HLA Class 1 antigen, HLA-A, HLA-B, HLA-A2, HLA-ABC, HLA-DR, HLA-DQ, HLA-DP, $\beta_2$-microglobulin, Fas (CD95/APO-1), FasL, P75, cathepsin D, neuroglandular antigen, pan-human cell antigen, motility antigens, proliferation markers, differentiation markers, drug resistance markers, angiogenesis markers, chemokine receptor markers, and invasion antigens.

4. The method according to claim 1, wherein the particles used in the method are coated with antibodies directed to tumor antigens that are markers reflecting characteristics of at least one of tumor cell proliferation, aggressiveness, metastasis, angiogenesis, chemotherapy resistance and apoptosis, and wherein the antigenic fingerprint is evaluated to determine a diagnosis.

5. The method according to claim 4, wherein the antibodies directed to tumor antigens are MOC31 anti EGP2 (anti-epithelial cell markers) antibody, anti-breast mucin (MUC1) antibody (BM7), 595, anti-EGF receptor (425.3), anti-erbB2 and anti-HWM melanoma antigen (9.2.27).

6. The method according to claim 1, wherein determining the antigenic fingerprint of the live target cells comprises profiling the antigenic determinants or receptors expressed on the cell membrane of the live target cells.

7. The method according to claim 6, wherein target cell characteristics that are biological markers of diagnostic, prognostic, and therapeutic value are registered.

8. The method according to claim 7, wherein the live target cells are malignant cells.

9. The method according to claim 7, wherein the biological markers are E-cadherin, EGFr, c-erbB2, IL-2 receptor, TNF receptor, EGP2, MUC1, MUC2 & 3, PSA, PSM, GA733.2, TAG72, 15-3 epitope, HMW 250000, gp 75/TRP-1, p95, MAG 1, 2, 3, TP 1 and TP 3 epitopes, ME1-14 epitope, Fas, FasL, p75, KAT-1, AMF, gp 120, MUC 19, TA99, MDR, MRP, VEGFr, bFGF, CCR, CXCR, uPAR, uPA, PAI-1, TIMP1 & 2, MMP9, stromelysins, cathepsin D and pan-human epitope.

10. A method according to claim 1 wherein at least one antibody selected from the 2 to 6 antibodies being directed against the independent antigenic determinants/receptors expressed on the same cells is conjugated to a magnetic or paramagnetic particle, and wherein the enrichment procedure enriches the cell suspensions for live target cells that are bound to the antibody conjugated to the magnetic or paramagnetic particle.

11. A method according to claim 10 wherein the enrichment procedure is an immunomagnetic enrichment procedure.

12. A method according to claim 10 wherein the antibodies being directed against the independent antigenic determinants/receptors expressed on the same cells comprise at least two antibodies that are conjugated to two visually different fluorescent particles.

13. A method according to claim 1 wherein the at least one fluorescent particle comprises a polystyrene latex fluorescent microsphere.

* * * * *